(12) United States Patent
Ter-Ovanesyan

(10) Patent No.: US 9,655,684 B2
(45) Date of Patent: May 23, 2017

(54) CATHETER GUIDANCE SYSTEM

(75) Inventor: Evgeny Ter-Ovanesyan, South San Francisco, CA (US)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 316 days.

(21) Appl. No.: 13/249,851

(22) Filed: Sep. 30, 2011

(65) Prior Publication Data

US 2013/0085448 A1  Apr. 4, 2013

(51) Int. Cl.
| A61F 7/12 | (2006.01) |
| A61B 90/00 | (2016.01) |
| A61B 17/00 | (2006.01) |
| A61B 18/00 | (2006.01) |
| A61B 18/14 | (2006.01) |
| A61B 34/20 | (2016.01) |

(52) U.S. Cl.
CPC .......... *A61B 90/06* (2016.02); *A61B 18/1492* (2013.01); *A61B 34/20* (2016.02); *A61B 2017/00084* (2013.01); *A61B 2017/00088* (2013.01); *A61B 2017/00092* (2013.01); *A61B 2017/00097* (2013.01); *A61B 2018/00714* (2013.01); *A61B 2018/00791* (2013.01); *A61B 2018/00797* (2013.01); *A61B 2018/00803* (2013.01); *A61B 2018/00809* (2013.01); *A61B 2018/00815* (2013.01); *A61B 2018/00821* (2013.01); *A61B 2018/00898* (2013.01); *A61B 2090/065* (2016.02)

(58) Field of Classification Search
CPC A61B 2017/00084; A61B 2017/00088; A61B 2017/00092; A61B 2017/00097; A61B 2018/00714; A61B 2018/00791; A61B 2018/00797

See application file for complete search history.

(56) References Cited

U.S. PATENT DOCUMENTS

| 4,852,027 | A | * | 7/1989 | Bowman et al. | 702/136 |
| 5,304,214 | A | * | 4/1994 | DeFord | A61B 18/082 604/916 |
| 5,496,311 | A | * | 3/1996 | Abele | A61B 17/22 606/28 |
| 6,547,757 | B1 | * | 4/2003 | Kranz et al. | 604/95.04 |

(Continued)

*Primary Examiner* — Laura Bouchelle
*Assistant Examiner* — Anh Bui
(74) *Attorney, Agent, or Firm* — Chen Yoshimura LLP

(57) ABSTRACT

A catheter guidance system and method for guiding a catheter through the bloodstream of the patient's cardiovascular system in a medical procedure. The catheter has a front tip with a heating element for slightly heating a media surrounding the front tip in a blood vessel of the patient's cardiovascular system, and two temperature measuring elements located adjacent to and in front and behind the heating element respectively for measuring temperatures in the media at their respective locations. A guidance device is coupled to the catheter for converting the heating power and temperature measurement signals to digital signals, processing the digital signals, and displaying guidance information indicative of the location of the front tip of the catheter relative to the blood vessel wall of the patient's cardiovascular system. The guidance information may be shown by an intuitive traffic light type display.

11 Claims, 2 Drawing Sheets

(56) References Cited

U.S. PATENT DOCUMENTS

| | | | |
|---|---|---|---|
| 6,632,183 B2* | 10/2003 | Bowman et al. | 600/564 |
| 2005/0015125 A1* | 1/2005 | Mioduski | A61B 18/1233 607/102 |
| 2005/0261611 A1* | 11/2005 | Makin | A61B 17/2202 601/2 |
| 2007/0233185 A1* | 10/2007 | Anderson | A61B 8/0833 606/213 |
| 2011/0087314 A1* | 4/2011 | Diederich et al. | 607/113 |
| 2011/0152854 A1* | 6/2011 | Govari | A61B 18/1492 606/33 |
| 2012/0226270 A1* | 9/2012 | Manwaring et al. | 606/31 |

\* cited by examiner

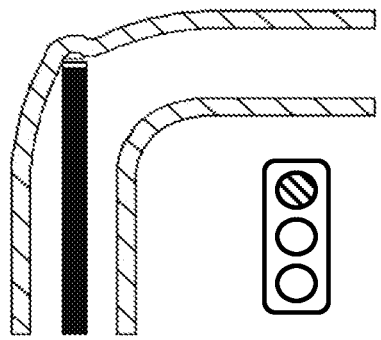
Fig. 2a
Fig. 2b
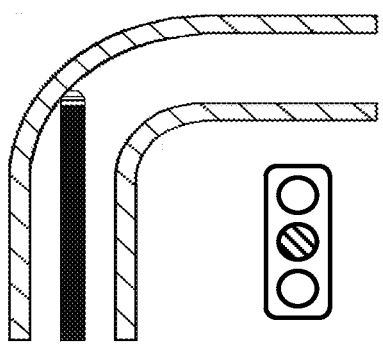
Fig. 3a
Fig. 3b
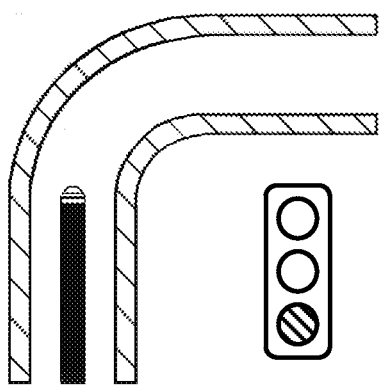
Fig. 4a
Fig. 4b

CATHETER GUIDANCE SYSTEM

BACKGROUND OF THE INVENTION

Field of the Invention

This invention relates generally to catheters and catheter guidance systems, and more particularly it relates to catheters and cardiac catheter guidance systems used in the bloodstream of a patient's cardiovascular system.

Description of Related Art

Cardiac catheterization technology is growing rapidly, and there is an increasing demand for simple and inexpensive cardiac catheters that are safe and easy to use.

The use of cardiac catheters has revolutionized the cardiology field. Several notable techniques have been developed based on the use of cardiac catheters, such as angiography which involves direct injection of X-ray contrast agent for better imaging, angioplasty which involves mechanical widening of an obstructed blood vessel with a balloon, and radio frequency (RF) ablation which involves burning a small area of the heart which cause cardiac arrhythmia.

However, navigating a cardiac catheter in a patient's cardiovascular system requires great skills of a highly trained interventional cardiologist. Any damage to the wall of a blood vessel should be minimized as the damage area might become a place where atherosclerotic plaque will start forming. Sometimes the catheter can perforate the wall of a blood vessel causing a life-threatening emergency. The risk of perforation is especially high in complex cases, such as for patients with heavily calcified blood vessels. A simple, inexpensive guidance system can help the interventional cardiologist to maneuver the cardiac catheter in the cardiovascular system while minimizing the risk of perforation to the wall of a blood vessel.

The most common catheter guidance technique currently in use is fluoroscopy (X-ray). The drawback is that X-ray exposure to the patient may be high during long, complex procedures. Other recently developed catheter-based imaging systems place magnets or force-contact sensors on a catheter, or utilize near-infrared imaging, for tracking the catheter movement in the cardiovascular system. These systems are rather complicated and quite expensive.

There is a need for a safe, simple and inexpensive catheter guidance system for assisting interventional cardiologist in navigating a catheter in a cardiovascular system, especially in complex cases, such as for patients with heavily calcified blood vessels.

SUMMARY

The present invention is directed to catheters and a guidance system for cardiac catheters.

An object of the present invention is to provide a guidance system or device for assisting a cardiologist to safely maneuver or navigate a cardiac catheter in a bloodstream of a patient's cardiovascular system.

Another object of the present invention is to provide a method for generating and displaying intuitive guidance information for assisting a cardiologist to safely maneuver or navigate a cardiac catheter in a bloodstream of a patient's cardiovascular system.

A further object of the present invention is to provide a cardiac catheter guidance system or device that is simple in design and construction, inexpensive to produce and easy to use in medical procedures.

To achieve these and/or other objects, as embodied and broadly described, the present invention provides a catheter guidance system, comprising a catheter for use in the bloodstream of a patient's cardiovascular system. The catheter comprises an elongated body with a front tip and a rear end; a heating element adjacent to the front tip for heating a media surrounding the front tip in a blood vessel of the patient's cardiovascular system; and at least two temperature measuring elements disposed adjacent to the heating element, one located in the front of the heating element between the front tip and the heating element and the other one located in the back of the heating element between the rear end and the heating element, for measuring temperatures in the media at respective locations of the two temperature measuring elements.

In one embodiment, the catheter guidance system also comprises a guidance device for guiding the catheter through the bloodstream of a patient's cardiovascular system in a medical procedure; and a cable electrically and electronically coupling the catheter and the guidance device for providing a heating power to the catheter and transmitting electronic signals of the heating power and the temperature measurements from the catheter to the guidance device.

According to embodiments of the present invention, the guidance device may comprise (a) a data processor for processing the electronic signals of the heating power and the temperature measurements and generating display signals indicative of the location of the front tip of the catheter relative to the blood vessel wall of the patient's cardiovascular system; (a) a controller for controlling the data processor and the heating power supplied to the catheter; and (c) a display unit coupled to the guidance device for displaying guidance information based on the display signals.

In another embodiment of the present invention, the guidance device may comprise (a) an analog/digital (A/D) converter for converting the heating power and temperature measurement signals to digital signals; (b) a data processor for processing the digital signals and generating display signals indicative of the location of the front tip of the catheter relative to the blood vessel wall of the patient's cardiovascular system; (c) a controller for controlling the functions of the A/D converter and the data processor and the heating power supplied to the catheter, and (d) a display unit coupled to the guidance device for displaying guidance information based on the display signals.

In embodiments of the present invention, the display unit may be an integral part of the guidance device or an independent unit.

In one exemplary embodiment of the present invention, the catheter guidance system further includes a power supply unit for supplying electrical power to the catheter through the cable.

In one preferred embodiment of the present invention, the guidance device keeps the heating power of the heating element of the catheter constant and calculates a temperature difference between temperature measurements in the media at the respective locations of the two temperature measuring elements of the catheter as an indication of the location of the front tip of the catheter relative to the blood vessel wall of the patient's cardiovascular system.

In another preferred embodiment of the present invention, the guidance device keeps the temperature difference between temperature measurements in the media at the respective locations of the two temperature measuring elements of the catheter constant and measures the heating power of the heating element of the catheter as an indication of the location of the front tip of the catheter relative to the blood vessel wall of the patient's cardiovascular system.

In a practical implementation of the present invention, the guidance information displayed on the display unit is a traffic light type display comprising: (a) a red light indicating that the front tip of the catheter is pressing through the blood vessel wall of the patient's cardiovascular system; (b) a yellow light indicating that the front tip of the catheter is contacting the blood vessel wall of the patient's cardiovascular system; and (c) a green light indicating that the front tip of the catheter is in the bloodstream in the blood vessel of the patient's cardiovascular system.

Also embodied and broadly described, the present invention provides a catheter guidance system for use in the bloodstream of a patient's cardiovascular system. The system comprises (a) a catheter having a body with a front tip and a rear end, a heating element disposed adjacent to the front tip for heating a media surrounding the front tip in a blood vessel of a patient's cardiovascular system, and two or more temperature measuring elements adjacent to the heating element for measuring temperatures located between the front tip and the heating element, and located between the rear end and the heating element respectively in the media; (b) a data processor for processing temperature measurement signals from the two or more temperature measuring elements and generating display signals indicative of the location of the front tip of the catheter relative to the blood vessel wall of the patient's cardiovascular system; (c) a controller for controlling the data processor and a heating power supplied to the catheter; and (d) a display unit for displaying guidance information based on the display signals.

In one embodiment of the present invention, the system may further comprises a cable electrically and electronically coupling the catheter and the guidance device for providing electrical power to the catheter and transmitting electronic signals of the heating power and the temperature measurements from the catheter to the guidance device.

Further embodied and broadly described, the present invention provides a method for guiding a catheter through a bloodstream of a patient's cardiovascular system, wherein the catheter has a rear end and a front tip with a heating element for heating a media surrounding the front tip in a blood vessel of the patient's cardiovascular system. In one embodiment, the method comprises: (a) generating temperature measurement signals from the catheter representing measured temperatures in the media at locations of the catheter adjacent to the heating element, in the front of the heating element between the front tip and the heating element, and in the back of the heating element between the rear end and the heating element respectively; (b) processing the temperature measurement signals and generating display signals indicative of a location of the front tip of the catheter relative to a blood vessel wall of the patient's cardiovascular system; and (c) displaying guidance information based on the display signals.

In one embodiment, the method further comprises the step of transmitting electronic signals of the temperature measurements to a guidance device. In another embodiment, it comprises the steps of (a) supplying electrical power to the catheter; and (b) controlling the heating power supplied to the catheter.

In one preferred embodiment of the present invention, the method further comprises the steps of: (a) keeping the heating power of the heating element of the catheter constant; and (b) calculating a temperature difference between the temperature measurements in the media at the locations in the front of the heating element and the back of the heating element respectively as an indication of the location of the front tip of the catheter relative to the blood vessel wall of the patient's cardiovascular system.

In another preferred embodiment of the present invention, the method further comprises (a) keeping the temperature difference constant between the temperature measurements in the media at the front of the heating element and the back of the heating element; and (b) measuring the heating power of the heating element of the catheter as an indication of the location of the front tip of the catheter relative to the blood vessel wall of the patient's cardiovascular system.

In a practical implementation of the present invention, the step of displaying guidance information further comprises the steps of (a) displaying a red light indicating that the front tip of the catheter is pressing through the blood vessel wall of the patient's cardiovascular system; (b) displaying a yellow light indicating that the front tip of the catheter is contacting the blood vessel wall of the patient's cardiovascular system; and (c) displaying a green light indicating that the front tip of the catheter is in the bloodstream in the blood vessel of the patient's cardiovascular system.

The catheter guidance system and method of the present invention can simplify a task of a cardiologist, allow other associate personnel who may not be necessarily as experienced as a highly trained specialist to perform the medical procedures in the bloodstream of a patient's cardiovascular system, and prevent potentially dangerous perforation of blood vessels, especially when blood vessel walls are brittle because of severe calcification. In addition, the catheter guidance system and method of the present invention are much safer than some conventional techniques such X-ray because there will be no exposure to ionizing radiation. Furthermore, the catheter guidance system of the present invention is simple and low cost comparing to conventional equipment for other techniques such as X-ray and ultrasound.

Additional features and advantages of the invention will be set forth in the descriptions that follow and in part will be apparent from the description, or may be learned by practice of the invention. The objectives and other advantages of the invention will be realized and attained by the structure and steps particularly pointed out in the written description and claims thereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

FIG. 2a is a schematic sectional diagram illustrating an exemplary situation where the catheter according to one embodiment of the present invention is pressing through a blood vessel wall of a patient's cardiovascular system.

FIG. 2b is a schematic diagram illustrating an exemplary display corresponding to the situation shown in FIG. 2a.

FIG. 3a is a schematic sectional diagram illustrating another exemplary situation where the catheter according to one embodiment of the present invention is contacting a blood vessel wall of a patient's cardiovascular system.

FIG. 3b is a schematic diagram illustrating an exemplary display corresponding to the situation shown in FIG. 3a.

FIG. 4a is a schematic sectional diagram illustrating another exemplary situation where the catheter according to one embodiment of the present invention is in the bloodstream in a blood vessel of a patient's cardiovascular system.

FIG. 4b is a schematic diagram illustrating an exemplary display corresponding to the situation shown in FIG. 4a.

DETAILED DESCRIPTION OF PREFERRED EMBODIMENTS

Figure 1:
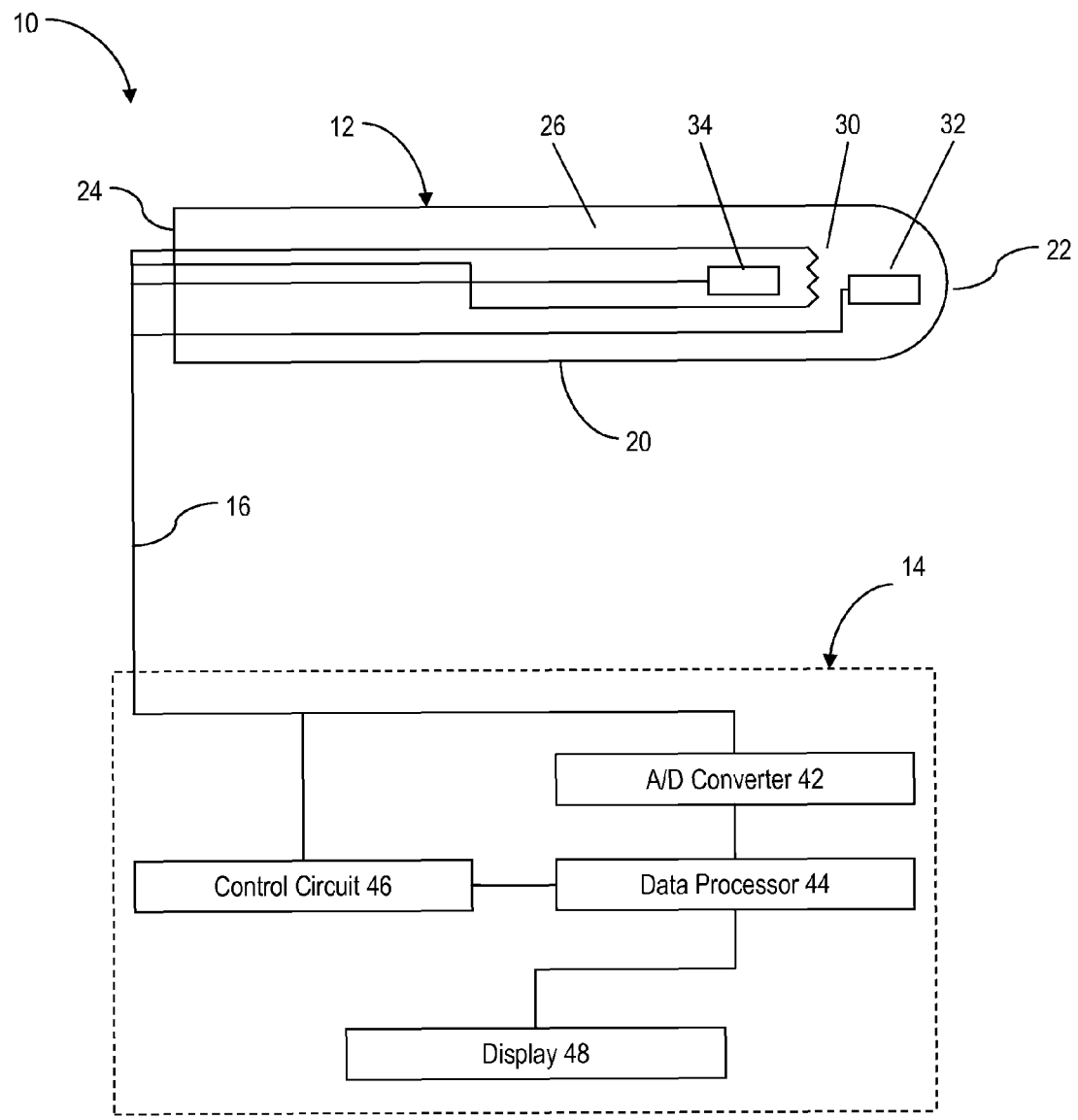
FIG. 1 is a schematic block diagram illustrating an exemplary catheter guidance system according to one embodiment of the present invention.

Embodiments of the present invention provide a catheter guidance system for medical procedures such as diagnostic procedures and interventional procedures, such as but not limited to radio-frequency (RF) ablation surgeries.

Referring to FIG. 1, it shows an exemplary catheter guidance system 10 according to one embodiment of the present invention. The catheter guidance system 10 includes a cardiac catheter 12 and a guidance device 14, coupled by a cable 16. Catheter 12 has an elongated body 20 with a front tip 22 and a rear end 24. Catheter 12 also has an internal chamber 26 that houses the internal functional components of catheter 12. For clarity purposes, only the components that relate to the design purpose and functions of the present invention are shown.

In one embodiment of the present invention, the catheter 12 of FIG. 1 has a small heating element 30 and two temperature measuring elements such as thermistors or thermocouples 32 and 34 located next to the heating element 30, with one temperature measuring element 32 in front of the heating element 30 and the other temperature measuring element 34 behind the heating element 30. The small heating element 30 and the two temperature measuring elements 32 and 34 are placed inside the chamber 26 and in close proximity of tip 22 of catheter 12. In one embodiment, they are placed on the inner surface of the chamber 26. The small heating element 30 heats tip 22 of catheter 12 to slightly higher than the body temperature, and the temperatures measured by the temperature measuring elements 32 and 34 provide information on the distance between the catheter tip 22 and the blood vessel wall. In one embodiment, the small heating element 30 heats tip 22 of catheter 12 to about 2-4 degrees above the body temperature.

It is understood that the heating element 30 and/or the two temperature measuring elements 32 and 34 are not necessarily located within a chamber of the catheter 12, but instead may be on the outside surface of the catheter 12, or otherwise exposed to and directly contacting the surrounding media (blood or tissue of the blood vessel wall) in a blood vessel of a patient's cardiovascular system. It is also understood that the number of temperature measuring elements may not be limited to two, and multiple temperature measuring elements may be used at different locations near the heating element.

The catheter 12 may be maneuvered in a patient's cardiovascular system either upstream (against the direction of the blood flow) or downstream (along the direction of the blood flow). By providing at least two temperature measuring elements 32 and 34 at the opposite sides of the heating element 30, the device of the embodiments of the present invention allows a measurement of temperature changes in both situations.

When catheter 12 is traveling upstream (i.e., against the direction of the blood flow), the blood surrounding the catheter 12 is flowing from the front tip 22 to the rear end 24 of the catheter 12. The media (blood or tissue of the blood vessel wall) first contacts the front temperature measuring element 32 before it is heated by the heating element 30, so the temperature measured by the front temperature measuring element 32 is close to the normal temperature of the media (e.g., the body temperature of the patient) which may be used as a base temperature. As the media contacts the heating element 30 is heated by the heating element 30, the heat is carried by the media towards the location of the rear temperature measuring element 34. The temperature measured by the temperature measuring element 34 will be higher than the base temperature because the media is heated by the heating element 30. If the thermal conductivity of the media is high (e.g., when the media is blood), then the heat loss from the location of the heating element 30 to the location of the rear temperature measuring element 34 will be great, and the temperature difference between the temperatures measured by the temperature measuring elements 32 and 34 will be small. Particularly at the center of the blood vessel and in the middle of the bloodstream, the velocity of blood flow is highest so that the thermal conductivity is also highest, which means that the heat loss from the location of the heating element 30 to the location of the rear temperature measuring element 34 is greatest, and the temperature difference between the temperatures measured by the temperature measuring elements 32 and 34 is smallest. On the other hand, if the thermal conductivity of the media is low (e.g., when the media is blood vessel wall), then the heat loss will be minimal from the location of the heating element 30 to the location of the rear temperature measuring element 34, and the temperature difference between the temperatures measured by the temperature measuring elements 32 and 34 will be large. Therefore, the difference between the two temperatures measured by the temperature measuring elements 32 and 34 can be used to indicate whether the catheter 12 is pressing through, contacting, or away from the blood vessel wall.

When catheter 12 is traveling downstream (i.e., along the direction of the blood flow), the blood surrounding the catheter 12 is flowing from the rear end 24 to the front tip 22 of the catheter 12. The media (blood or tissue of the blood vessel wall) first contacts the rear temperature measuring element 34 before it is heated by the heating element 30, so the temperature measured by the rear temperature measuring element 34 is close to the normal temperature of the media (e.g., the body temperature of the patient) which may be used as a base temperature. As the media contacts the heating element 30 is heated by the heating element 30, the heat is carried by the media towards the location of the front temperature measuring element 32. The temperature measured by the temperature measuring element 32 will be higher than the base temperature because the media is heated by the heating element 30. If the thermal conductivity of the media is high (e.g., when the media is blood), then the heat loss from the location of the heating element 30 to the location of the front temperature measuring element 32 will be great, and the temperature difference between the temperatures measured by the temperature measuring elements 32 and 34 will be small. Particularly at the center of the blood vessel and in the middle of the bloodstream, the velocity of blood flow is highest so that the thermal conductivity is also highest, which means that the heat loss from the location of the heating element 30 to the location of the front temperature measuring element 32 is greatest, and the temperature difference between the temperatures measured by the temperature measuring elements 32 and 34 is smallest. On the other hand, if the thermal conductivity of the media is low (e.g., when the media is blood vessel wall), then the heat loss will be minimal from the location of the heating element 30 to the location of the front temperature measuring element 32, and the temperature difference between the temperatures measured by the temperature measuring elements 32 and 34 will be large. Again, the difference between the two temperatures measured by the temperature measuring elements 32 and 34 can be used to indicate whether the catheter 12 is pressing through, contacting, or away from the blood vessel wall.

Accordingly, the catheter design of the embodiments of the present invention with at least two temperature measuring elements 32 and 34, one located in front of the heating element 30 and the other located behind the heating element 30, enables the embodiments of the present invention to handle both situations: whether the catheter is maneuvered to travel upstream or downstream in the blood vessel of a patient's cardiovascular system.

The small heating element 30 and temperature measuring elements 32 and 34 are all coupled to the cable 16 which leads from the end 24 of the catheter to the guidance device 14. Electrical power to the healing element 30 may be provided by guidance device 14 through a wiring element of cable 16. In addition, the electronic signals from the temperature measuring elements 32 and 34 and heating element 30 are transmitted to the guidance device 14 through the same or additional wiring element of cable 16.

The signals from the temperature measuring elements 32 and 34 are received, analyzed and processed by the guidance device 14. The guidance device 14 may include an analog/digital (A/D) converter 42 for converting the analog temperature measurement signals to digital signals, which are then processed by a data processor 44. Alternatively, the analog signals may be processed directly by the data processor. The guidance device also includes a control circuit 46 for control the functions of the A/D converter 42 and data processor 44, and may also control the heating power of the heating element 30 of the catheter 12. The guidance device may further includes a power converter/supply unit (not shown) that converts alternate current (AC) power to direct current (DC) power and supply electrical power to the catheter 12.

The analog data of heating power may also be transmitted to the A/D converter 42 for further processing and analysis by the data processor 44. There are a number of options on how the guidance device 14 controls the heating element 30 and collects and analyzes the temperature measurement of the temperature measuring element 32 and 34. Therefore there are a number of different algorithms that may be applied to process the data.

For example, the guidance device may keep the heating power of the heating element 30 constant, and calculate the temperature difference in the media between the respective locations of the two temperature measuring elements 32 and 34. The data processor then applies an algorithm wherein the temperature difference between temperature measuring elements 32 and 34 is reversely proportional to the heat loss in the media near the tip 22 of the catheter 12. As discussed earlier, in this scenario a large temperature difference will indicate that the media is blood vessel wall, while a small temperature difference will indicate that the media is blood, and an even smaller temperature difference will indicate that the catheter tip 22 is further away from the blood vessel wall, i.e., safely located near the middle or center of the blood vessel of the patient's cardiovascular system.

Alternatively the guidance device may keep the temperature difference in the media between the respective locations of the two temperature measuring elements 32 and 34 constant, and measure the heating power of the heating element 30. The data processor then applies an alternative algorithm wherein the heating power of the heating element 30 is proportional to the heat loss in the media near the tip 22 of the catheter 12. As discussed earlier, blood has a higher heat loss than blood vessel wall, and the blood flow in the middle of blood vessel has the highest heat loss. Therefore, in this alternative scenario a low heating power (proportional to low heat loss) will indicate that the media is blood vessel wall, while a higher heating power (proportional to high heat loss) will indicate that the media is blood, and an even higher heating power (proportional to even higher heat loss) will indicate that the catheter tip 22 is further away from the blood vessel wall, i.e., safely located near the middle or center of the blood vessel of the patient's cardiovascular system.

After the signals are analyzed, the data processor 44 will generate and send display signals to a display 48 for visually displaying guidance information indicative of the location of the catheter tip 22 relative to the blood vessel wall as an aid to an interventional cardiologist performing RF ablation. The information displayed may be represented by, for example, a traffic light type of display to provide an easy and intuitive guidance.

Referring to FIGS. 2a and 2b, when the signals processed by the data processor 44 indicate that the catheter is pressing through the blood vessel wall as shown in FIG. 2a, the display 48 may display a red light to indicate that the catheter tip 22 is pressing through the wall of a blood vessel. The red light provides a visual warning of a high perforation risk.

Referring to FIGS. 3a and 3b, when the signals processed by the data processor indicate that the catheter is contacting the blood vessel wall as shown in FIG. 3a, the display 48 may display a yellow light to indicate that the catheter tip 22 is contacting the wall of a blood vessel. The yellow light provides a visual warning of a potential perforation risk.

Referring to FIGS. 4a and 4b, when the signals processed by the data processor indicate that the catheter is in the middle of a blood vessel away from the blood vessel wall as shown in FIG. 4a, the display 48 may display a green light to indicate that the catheter tip 22 is safely away from the wall of a blood vessel. The green light provides a visual indication of safe maneuvering of the catheter 12.

It is noted that other types of display may be utilized to provide a visual and intuitive guidance to an interventional cardiologist performing a medical procedure. It is also noted that the display 48 may be an integral part of the guidance device 14, or a separate display unit coupled to the guidance device 14. It is further noted that the guidance device 14 may be incorporated into and become a part of an existing RF ablation or catheter controller device.

The catheter guidance system and method of the embodiments of the present invention have many advantages. They provide a novel way to monitor the distance between the tip of an RF ablation catheter and the blood vessel wall for safely navigating the catheter in the bloodstream. They also provide an intuitive visual indication to an interventional cardiologist that helps him or her to avoid potentially dangerous perforation of blood vessels, especially when blood vessel walls are brittle because of severe calcification. They simplify a task of an interventional cardiologist and might allow associate personnel with less experience to perform such procedures. They also improve the success rate of a RF ablation procedure which highly depends on the contact area between the catheter tip and the blood vessel wall. They further increase the safety of medical procedures involving catheters by avoiding exposure to ionizing radiation associated with X-ray, and also reduces the costs of such procedures as compared to X-ray and ultrasound. Moreover, the guidance system and method of the embodiments of the present invention can also be used in other applications such as endoscopy, urology, gynecology and pulmonology.

It will be apparent to those skilled in the art that various modification and variations can be made to the system and method of the present invention without departing from the spirit or scope of the invention. Thus, it is intended that the present invention cover modifications and variations that come within the scope of the appended claims and their equivalents.

What is claimed is:

1. A catheter for use in a bloodstream of a patient's cardiovascular system, comprising:
   an elongated body with a front tip and a rear end;
   a heating element with controllable and variable heating power including at least three different non-zero heating power levels, disposed adjacent to the front tip for heating a media surrounding the front tip in a blood vessel of the patient's cardiovascular system;
   two temperature measuring elements disposed adjacent to the heating element, including a first temperature measuring element located between the front tip and the heating element without any other heating element located between the first temperature measuring element and the front tip, and a second temperature measuring element located between the rear end and the heating element, for measuring temperatures in the media at respective locations of the two temperature measuring elements;
   a guidance device for guiding the catheter through the bloodstream of a patient's cardiovascular system in a medical procedure; and
   a cable electrically and electronically coupling the catheter and the guidance device for providing a heating power to the catheter and transmitting electronic signals of the heating power and the temperature measurements from the catheter to the guidance device;
   wherein the guidance device comprises:
      a data processor for processing the electronic signals of the heating power and the temperature measurements and generating signals indicative of a distance between the front tip of the catheter and the blood vessel wall of the patient's cardiovascular system based on a relationship between the heating power and a temperature difference between temperatures measured by the two temperature measuring elements, the signals including multiple signal values that correspondingly indicate multiple non-zero distance values;
      a display unit for displaying guidance information based on the signals generated by the data processor;
   wherein the guidance information displayed on the display unit is a traffic light type display comprises:
      a red light indicating that the front tip of the catheter is pressing through the blood vessel wall of the patient's cardiovascular system;
      a yellow light indicating that the front tip of the catheter is contacting the blood vessel wall of the patient's cardiovascular system; and
      a green light indicating that the front tip of the catheter is in the bloodstream in the blood vessel of the patient's cardiovascular system.

2. The system according to claim 1, wherein the guidance device keeps the heating power of the heating element of the catheter constant and calculates a temperature difference between temperature measurements in the media at the respective locations of the two temperature measuring elements of the catheter as an indication of the distance between the front tip of the catheter and the blood vessel wall of the patient's cardiovascular system.

3. The system according to claim 1, wherein the guidance device keeps a temperature difference between temperature measurements in the media at the respective locations of the two temperature measuring elements of the catheter constant and measures the heating power of the heating element of the catheter as an indication of the distance between the front tip of the catheter and the blood vessel wall of the patient's cardiovascular system.

4. A system comprising:
   a catheter having a body with a front tip and a rear end, a heating element with controllable heating power disposed adjacent to the front tip for heating a media surrounding the front tip in a blood vessel of a patient's cardiovascular system, and two or more temperature measuring elements adjacent to the heating element for measuring temperatures located between the front tip and the heating element, and located between the rear end and the heating element respectively in the media;
   a guidance device having a data processor for processing temperature measurement signals from the two or more temperature measuring elements and generating signals indicative of a distance between the front tip of the catheter and the blood vessel wall of the patient's cardiovascular system based on a temperature difference between temperatures measured by the two temperature measuring elements, the signals including multiple signal values that correspondingly indicate multiple non-zero distance levels; and
   a display unit for displaying guidance information as a traffic light type display that includes:
      a red light indicating that the front tip of the catheter is pressing through the blood vessel wall of the patient's cardiovascular system;
      a yellow light indicating that the front tip of the catheter is contacting the blood vessel wall of the patient's cardiovascular system; and
      a green light indicating that the front tip of the catheter is in the bloodstream in the blood vessel of the patient's cardiovascular system.

5. The system of claim 4, wherein the catheter includes two temperature measuring elements, including a first temperature measuring element located between the front tip and the heating element without any other heating element located between the first temperature measuring element and the front tip, and a second temperature measuring element located between the rear end and the heating element, for measuring temperatures in the media at respective locations of the two temperature measuring elements.

6. The system according to claim 4, further comprising a cable electrically and electronically coupling the catheter and the guidance device for providing electrical power to the catheter and transmitting electronic signals of a heating power and the temperature measurements from the catheter to the guidance device.

7. The system according to claim 4, wherein the guidance device keeps a heating power of the heating element of the catheter constant and calculates a temperature difference between the temperature measurements in the media at the respective locations of the temperature measuring elements of the catheter as an indication of the distance between the front tip of the catheter and the blood vessel wall of the patient's cardiovascular system.

8. The system according to claim 4, wherein the guidance device keeps a temperature difference between temperature measurements in the media at the respective locations of the temperature measuring elements of the catheter constant and measures a heating power of the heating element of the catheter as an indication of the distance between the front tip of the catheter and the blood vessel wall of the patient's cardiovascular system.

9. A catheter for use in a bloodstream of a patient's cardiovascular system, comprising:
   an elongated body with a front tip and a rear end;
   a heating element with controllable heating power adjacent to the front tip for heating a media surrounding the front tip in a blood vessel of the patient's cardiovascular system, wherein the heating element is controllable to heat the front tip to about 2-4° C. above a body temperature of the patient for a controlled period of time;
   two temperature measuring elements disposed adjacent to the heating element, a first temperature measuring element located between the front tip and the heating element and a second temperature measuring element located between the rear end and the heating element, for measuring temperatures in the media at respective locations of the two temperature measuring elements;
   a guidance device for guiding the catheter through the bloodstream of a patient's cardiovascular system in a medical procedure; and
   a cable electrically and electronically coupling the catheter and the guidance device for providing a heating power to the catheter and transmitting electronic signals of the heating power and the temperature measurements from the catheter to the guidance device;
   wherein the guidance device comprises:
      a data processor for processing the electronic signals of the heating power and the temperature measurements and generating signals indicative of a distance between the front tip of the catheter and the blood vessel wall of the patient's cardiovascular system based on a relationship between the heating power and a temperature difference between temperatures measured by the two temperature measuring elements, the signals including multiple signal values that correspondingly indicate multiple non-zero distance values; and
      a display unit for displaying guidance information based on the signals generated by the data processor;
   wherein the guidance information displayed on the display unit is a traffic light type display comprises:
      a red light indicating that the front tip of the catheter is pressing through the blood vessel wall of the patient's cardiovascular system;
      a yellow light indicating that the front tip of the catheter is contacting the blood vessel wall of the patient's cardiovascular system; and
      a green light indicating that the front tip of the catheter is in the bloodstream in the blood vessel of the patient's cardiovascular system.

10. The system according to claim 9, wherein the guidance device keeps the heating power of the heating element of the catheter constant and calculates a temperature difference between temperature measurements in the media at the respective locations of the two temperature measuring elements of the catheter as an indication of the distance between the front tip of the catheter and the blood vessel wall of the patient's cardiovascular system.

11. The system according to claim 9, wherein the guidance device keeps a temperature difference between temperature measurements in the media at the respective locations of the two temperature measuring elements of the catheter constant and measures the heating power of the heating element of the catheter as an indication of the distance between the front tip of the catheter and the blood vessel wall of the patient's cardiovascular system.

* * * * *